(12) United States Patent
Pal et al.

(10) Patent No.: US 12,291,735 B2
(45) Date of Patent: May 6, 2025

(54) METHOD FOR THE PRODUCTION OF ETHANOL FROM CORN FIBERS

(71) Applicant: PRAJ INDUSTRIES LIMITED, Pune (IN)

(72) Inventors: Siddhartha Sourav Pal, Pune (IN); Prasanna Sham Pai, Pune (IN); Ajit Prabhakar Deshmukh, Pune (IN); Sandip Uttamrao Nalwade, Pune (IN); Nilesh Ankush Borage, Pune (IN); Ghanshyam Baburao Deshpande, Pune (IN); Pramod Shankar Kumbhar, Pune (IN)

(73) Assignee: PRAJ INDUSTRIES LIMITED (IN)

( * ) Notice: Subject to any disclaimer, the term of this patent is extended or adjusted under 35 U.S.C. 154(b) by 584 days.

(21) Appl. No.: 17/619,360

(22) PCT Filed: Jun. 8, 2020

(86) PCT No.: PCT/IN2020/050505
§ 371 (c)(1),
(2) Date: Dec. 15, 2021

(87) PCT Pub. No.: WO2020/261291
PCT Pub. Date: Dec. 30, 2020

(65) Prior Publication Data
US 2022/0298532 A1    Sep. 22, 2022

(30) Foreign Application Priority Data

Jun. 24, 2019 (IN) .............................. 201921024907

(51) Int. Cl.
*C12P 7/14* (2006.01)

(52) U.S. Cl.
CPC ..................................... *C12P 7/14* (2013.01)

(58) Field of Classification Search
None
See application file for complete search history.

(56) References Cited

U.S. PATENT DOCUMENTS

| | | | |
|---|---|---|---|
| 7,727,726 B2 | 6/2010 | Cates et al. | |
| 2022/0298532 A1* | 9/2022 | Pal | C12P 7/06 |

FOREIGN PATENT DOCUMENTS

EP    2421984 A1    2/2012

* cited by examiner

*Primary Examiner* — Hope A Robinson
(74) *Attorney, Agent, or Firm* — Billion & Armitage

(57) ABSTRACT

Method for the production of ethanol from corn fibers. Invention relates to a process for the preparation of ethanol from a corn fiber containing feedstock by using a set of process steps specifically identified for the treatment of the said feedstock. It particularly relates to the use of a soaking followed by mix acid and enzyme treatment that release fermentable C5 and C6 sugars from said feedstock. It further relates to using a recombinant yeast to convert both C5 and C6 sugars to ethanol.

18 Claims, 2 Drawing Sheets

METHOD FOR THE PRODUCTION OF ETHANOL FROM CORN FIBERS

This application claims the benefit of and priority to Indian Patent Application number 201921024907 titled "METHOD FOR THE PRODUCTION OF ETHANOL FROM CORN FIBERS", filed Jan. 1, 2021, the contents of which are incorporated by reference herein.

FIELD OF THE INVENTION

The invention relates to a process for the preparation of ethanol from a corn fiber containing feedstock by using a set of process steps specifically developed for the treatment of the said feedstock. It particularly relates to the use of an acid soaking step followed by mix acid and enzyme treatments that release fermentable C5 and C6 sugars from said feedstock. It further relates to using a recombinant yeast to convert both C5 and C6 sugars to ethanol.

BACKGROUND

The conversion of starch to ethanol is rapidly expanding industry. The corn or maize seeds are a major source of starch for the ethanol industry. Ethanol has widespread applications as an industrial chemical, a gasoline additive or a liquid fuel by itself, besides in potable ethanol and liquor industry. However, the corn seeds also contain about 15% non-starch sugar polymers like hemicellulose and cellulose. The conventional starch to ethanol processes cannot use these non-starch sugar polymers like hemicellulose and cellulose present in corn fiber due to inherent problems of converting hemicellulose and cellulose polymers to fermentable sugars and its subsequent conversion to ethanol by natural yeasts.

A conventional process for ethanol production from starch is milling to extract starch from corn, which is further cooked, liquefied, saccharified by a mixture of enzymes ($\alpha$-amylase and glucoamylase) and fermented to produce ethanol. During this process, starch portion of the grain are used for the ethanol production and a large amount of distiller's soluble portion is generated as a co-product also called "whole stillage." It has about 87% of moisture content. This whole stillage is a by-product which is dehydrated and used as a valuable feedstock for livestock, poultry, and fish. The removal of water from whole stillage is costly in terms of energy (700-3000 kJ/kg of water, i.e., about 30% energy requirements of the entire plant may be required) and involves the use of equipment that contributes to capital and operating expenses. This whole stillage also includes fiber, oil, proteins, non-fermentable starch along with inhibitors, cellulose, hemicellulose, and so the resultant feed is difficult for monogastric animals to digest. Hence the use of the whole stillage for additional ethanol production is useful approach for total economics of corn to ethanol process.

Invention disclosed herein uses corn fiber wet cake (CFWC) for ethanol production. The CFWC is part of a whole stillage, which is obtained after the distillation of ethanol from beer or ferment, remaining after separation of liquid by centrifugation or filtration. The said liquid contains between 10% and 30% soluble proteins along with other things that inhibit hydrolysing enzymes. The CFWC is used for additional ethanol production from corn fibers and also addresses the problems like: 1) increased operating cost because of high moisture content of whole stillage; 2) the possibility of degradation of soluble proteins; and 3) low efficiency of ethanol production from whole stillage due to high concentrations of soluble proteins and inhibitors in the whole stillage.

BRIEF DESCRIPTION OF DRAWINGS

These and other features, aspects, and advantages of the present invention will become better understood when the following detailed description is read with reference to the accompanying drawings, wherein.

DETAILED DESCRIPTION OF THE INVENTION

Figure 1:
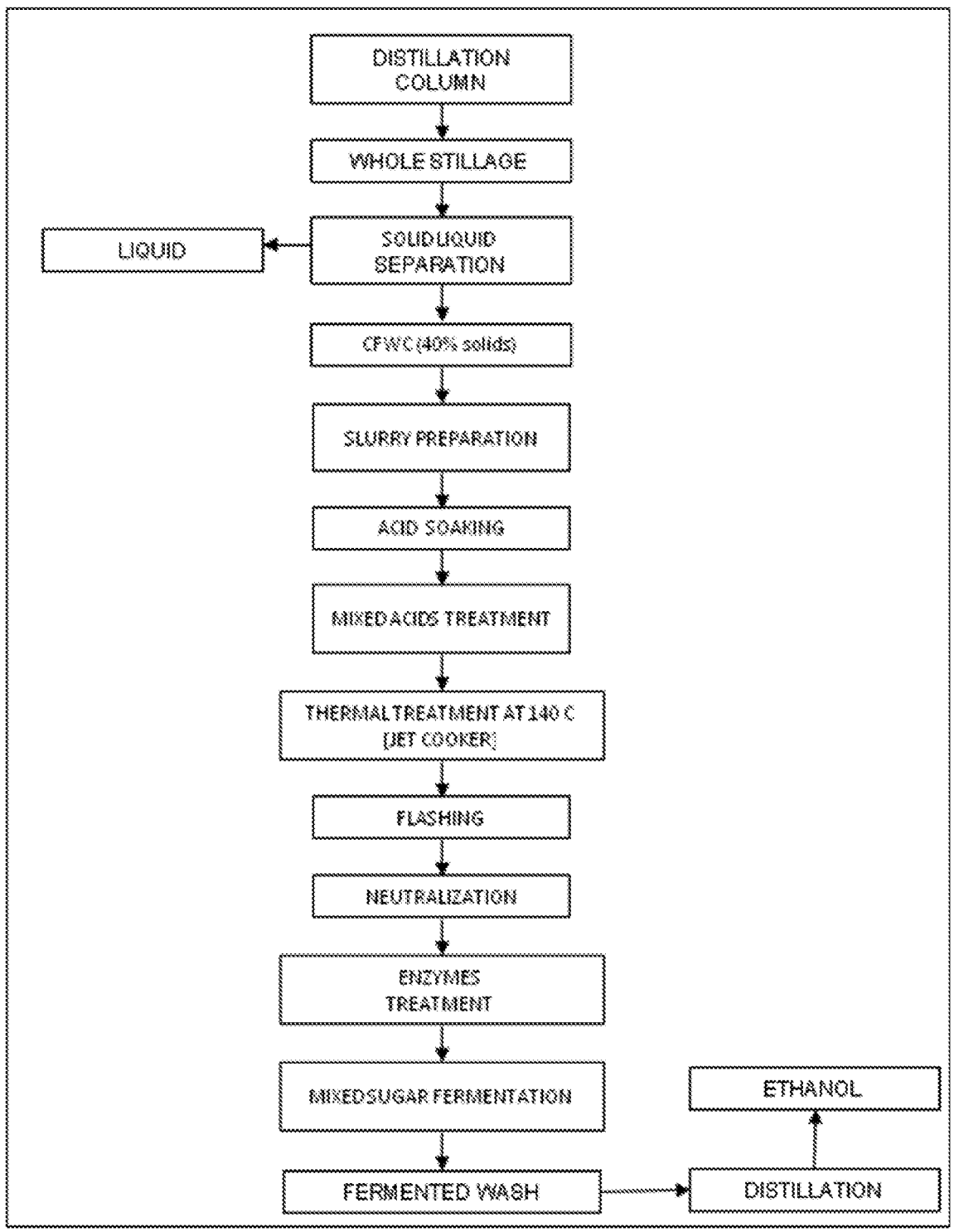
FIG. 1 depicts a schematic diagram of mass flow during the production of ethanol from a corn fiber wet cake. Different elements of the process are identified and directional movement and streams formed during the process are shown to describe the features of one embodiment of the present invention.

In one embodiment of the present invention, as illustrated in FIG. 1 said process includes nine steps, namely: 1) feedstock preparation and storage; 2) slurry preparation; 3) soaking of slurry; 4) preheating with mixture of acids; 5) thermal treatment; 6) flashing and heat recovery; 7) enzyme treatment; 8) co-fermentation; and 9) distillation and recovery of ethanol. Each step has one or more elements for performing specific function as required for production of ethanol from corn fiber wet cake. A person skilled in the art may appreciate different variations and/or combinations of these elements that may be used to perform the objects of the invention disclosed herein.

1. Feedstock Preparation and Storage

In corn to ethanol or beer production process, corn is first milled for mashing process followed by liquefaction of starch therein using enzymes and slurry is prepared. Said slurry is fermented further by means of yeast. Said fermented stream is also called beer and is further subjected to distillation to recover ethanol. The material remaining at the bottom of said distillation column is recovered, which is commonly referred as whole stillage. Said whole stillage comprises about 20% w/w of solids is subjected to removal of liquid by decantation or centrifugation to get a cakey material with about 40% w/w solids, which is called corn fiber wet cake (CFWC), which is the feedstock for the process of ethanol production. Said liquid stream recovered is sent to evaporators to produce concentrated protein rich stream. The CFWC is stored in storage tank for further use. Its composition is cellulose about 10% to about 15%, xylan about 12% to about 16%, arabinan about 3% to about 6% and starch about 0.5% to about 10% by weight. A typical composition is listed is in TABLE 1. The CFWC used in this disclosure is extracted from the whole stillage obtained from the corn-based ethanol plants located in the United States of America and Europe. Three sources of whole stillage are used to cover the diversity of the feedstock.

TABLE 1

CORN FIBER WET CAKE COMPOSITION

| Parameters | Unit | Value |
| --- | --- | --- |
| Total solids | % w/w | 30-40 |
| Cellulose | % w/w | 10-15 |
| Starch | % w/w | 0.5-10 |
| Xylan | % w/w | 12-16 |
| Arabinan | % w/w | 3-6 |
| Crude protein | % w/w | 34-40 |
| Ash | % w/w | 2-4 |
| Water extractives | % w/w | 5-10 |
| Ether extractives | % w/w | 5-10 |

2. Slurry Preparation

The flowability of CFWC is optimized between 20% and 25% of total solids by weight on adding water or recycled water forming a slurry for further treatment. Said slurry is used for soaking under acidic conditions followed by thermo chemical acid pre-treatment which hydrolyzes the complex cellulose, hemicellulose and starch structures into the glucose, xylose and arabinose molecules.

3. Soaking of Slurry

Figure 2:
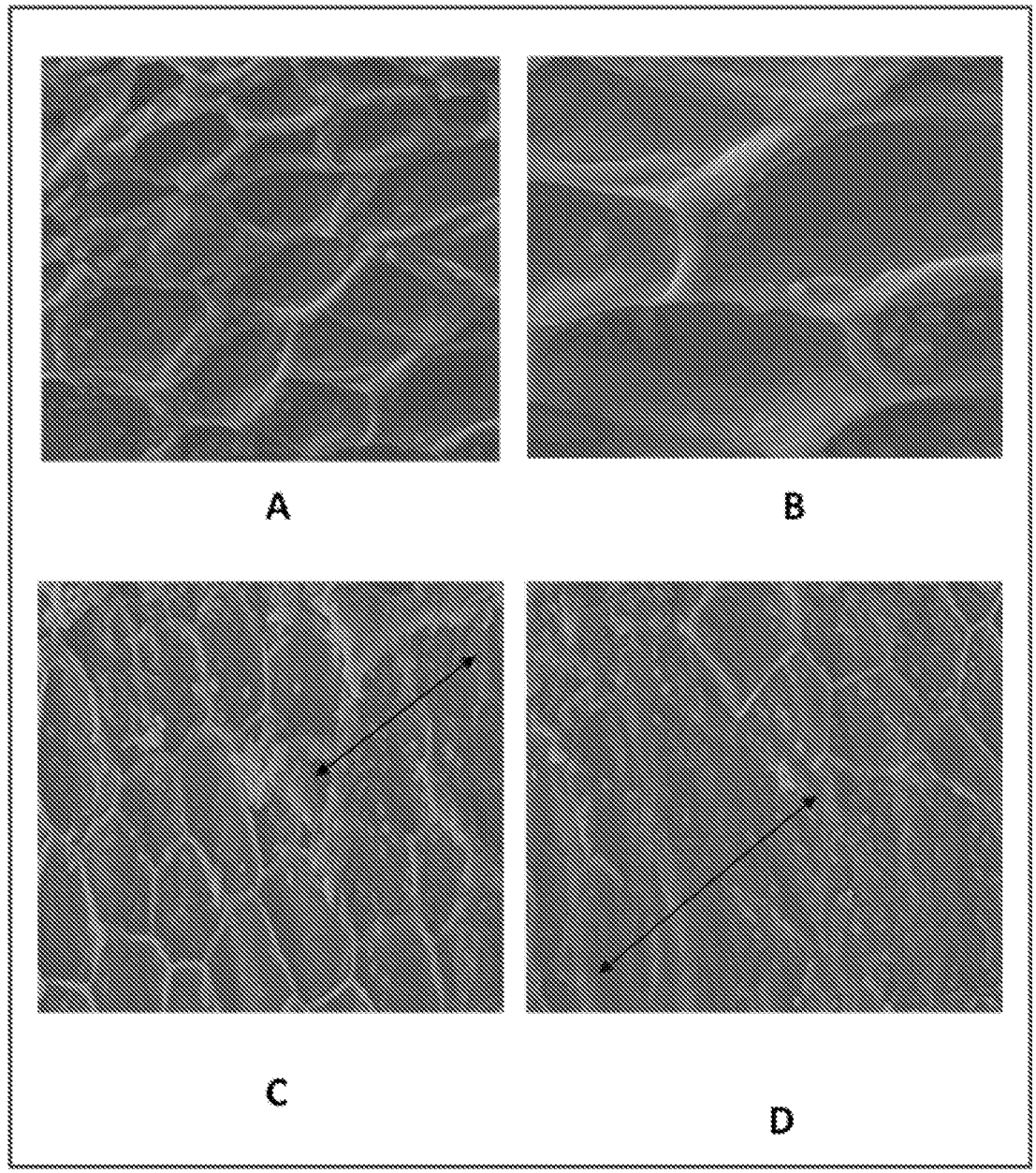
FIG. 2 depicts the images of CFWC in the native state and soaked in acid for about 30 min. This depicts the morphological differences between the CFWC in untreated native state and the CFWC after acid soaking. The SEM images at two different resolutions show the cell wall structures before and after said soaking. The FIGS. 2A (at 20μ) and 2B (at 50μ) show the intact cell wall structure of native CFWC. The FIG. 2C (at 20μ) and 2D (at 50μ) show the disrupted cell walls of CFWC after said soaking (indicated by arrows).

Next, said slurry is soaked into about 0.5% to about 2% of sulfuric acid (on dry weight basis) at desire temperature and time, more particularly between 30° C. and 60° C. temperature for about 20 to about 40 minutes to form an acidic slurry. Said soaking procedure disrupts about 40% cell wall structures and increases the porosity and penetration of acids in the complex polysaccharide structures which increases the overall sugar yield at the final stage. Said effect of soaking is described in Example 5 and FIG. 2.

4. Preheating with Mixture of Acids

Next, the temperature of said acidic slurry is increased to between about 70° C. to about 90° C. using low pressure steam and then between 0.5% and 4% by weight of a mixture of acids is added to it. Said mixture of acids contains sulphuric and phosphoric acids, wherein the concentration of phosphoric acid is between 20% and 40% by weight. Here said stream is treated at about 70° C. for between 5 min and 40 min to form a second acidic slurry. Here, phosphoric acid is used as decrystallizing agent to reduce the crystallinity of cellulose fibers. Further said this acid treatment helps to adjust the pH before the thermal treatment.

5. Thermal Treatment

Said second acidic slurry is cooked in a jet cooker at desired temperature and time, more particularly said second acidic slurry is passed through a jet cooker wherein temperature between 140 and 150° C. and pressure between 3 and 5 bar(g) is maintained for about 5 to about 40 min to prepare a pretreated stream. This treatment breakdowns the lignin carbohydrate complex and depolymerizes hemicellulose forming a pretreated stream. Said pretreated stream comprises glucose about 0.2% to about 2.5%, xylose about 1.5% to about 3.5% and arabinose about 0.5% to about 1.5% by weight. These hydrolysis steps from soaking to thermal treatment increases the efficiency of sugar recovery from the polymers present in CFWC. The efficiency of xylan to xylose conversion is about 70 to 80% and the efficiency of arabinan to arabinose is about 70 to 90%.

6. Flashing And Heat Recovery

Next, said pretreated stream is subjected to flashing and energy recovery in a flash tank. The two-step flashing is performed to reduce pretreated stream's temperature from about 140-150° C. to about 50-55° C. and concentrate it under atmospheric pressure and excess heat is recovered. Next, further flash treatment is performed under vacuum to reduce the temperature of material to about 50 to 55° C. for enzyme treatment step forming a concentrated stream. The excess heat recovered is used for preheating slurry or in distillation units.

7. Enzyme Treatment

The pH of said concentrated stream is neutralized using sodium hydroxide and it is subjected to enzymatic hydrolysis to release fermentable sugars. Said enzyme hydrolysis is carried out using desired quantities of glucoamylase, cellulases and hemicellulases for desired temperature and time to form an enzyme treated stream. During enzyme treatment temperature is maintained at between 45° C. and 6° C. for between 30 and 72 h. Said enzyme treated stream comprises both C5 and C6 sugars. It comprises glucose between about 1% to about 4%, xylose between about 1.5% to about 3.5% and arabinose between about 0.5% to about 1.5% by weight. In this enzyme hydrolysis step the conversion of cellulose and starch to sugar is about 80 to 85%.

8. Co-Fermentation

Next, said enzyme treated stream is fermented with a recombinant yeast *Saccharomyces cerevisiae* strain using preformented seed for about 36 to 72 h at about 32° C. forming a second fermented stream. During fermentation desired quantity of glucoamylase is added for the conversion of remaining starch to glucose. Said yeast strain is capable fermenting glucose, xylose and arabinose to ethanol. The efficiency of xylose and glucose to ethanol is about 80 to 90% and the efficiency of arabinose to ethanol is about 50-60%.

9. Distillation and Recovery of Ethanol and Second Stream:

Said second fermented stream is further distilled out to recover ethanol from it. The bottom stream generated at this stage contains between 30% and 60% protein by weight, inactivated yeast, etc, which is used as an animal feed component.

Advantages:
1) The process uses 20 to 25% w/w solids during pre-treatment procedure.
2) The process includes soaking treatment which increases the conversion efficiency of cellulose, xylan and arabinan to its respective monomeric sugars.
3) The combination of soaking and mixed acids treatment for corn fiber wet cake increases the overall efficiency of hydrolysis.
4) Jet cooker system reduces the capital investment and improves the heat transfer.
5) Ethanol titre in the second fermented stream for distillation is increased by 33% which increases the efficiency and reduces the overall cost of production of ethanol.
6) Co-fermentation of glucose, arabinose and xylose is achieved by modified yeast which substantially reduced the operational and capital expenses of two different fermentation procedures.
7) Second bottom stream or wet cake having between 30% and 60% protein and inactivated yeast is used further as an animal feed component.

Examples provided below give wider utility of the invention without any limitations as to the variations that may be appreciated by a person skilled in the art. A non-limiting summary of various experimental results is given in the examples, which demonstrate the advantageous of soaking, mixed acid enzymes with engineered yeast to produce ethanol from wet cake.

Example 1

A batch of about 200 kg corn fiber wet cake (CFWC) with total solids about 35% (that was about 70 kg of solids) was used as a feedstock. This feedstock was diluted with about 150 kg process water to make a slurry with about 20% w/w of solids comprising about 13.11% cellulose, about 11.18% xylan, about 9.22% arabinan and about 1.8% starch. The temperature of said slurry was raised to about 70° C. using low pressure steam. Next, said slurry was mixed with about 1.45 kg of sulfuric acid and about 0.8 kg of phosphoric acid, the final amount of sulfuric acid was about 2% w/w and phosphoric acid was about 1% w/w) and treated at about 70° C. for about 30 min forming an acidic slurry. Next, said acidic slurry was passed through a jet cooker wherein temperature and pressure were maintained for about 145° C. and about 3.3 bar(g) for about 26 min forming a pretreated stream. Post pre-treatment about 328 kg pretreated stream was obtained having pH of about 1.2 with about 20.1% w/w of total solids containing about 0.3% w/w of glucose, about 1.5% w/w of xylose, about 0.9% w/w of arabinose, about 0.22% w/w of acetic acid, about 0.03% w/w of HMF and about 0.03% w/w of furfural. The conversion of xylan to xylose, arabinan to arabinose and cellulose and starch to glucose in pre-treatment were about 56%, 40% and 9% respectively. Then said pretreated stream was subjected to flashing to reduce temperature forming a concentrated stream. The pH of said concentrated stream was adjusted to about 5.5 using 4020 ml 40% w/v of sodium hydroxide. Then said concentrated stream was treated with about 0.98 g of Glucoamylase (0.75 kg/ton of starch) and about 211 g of cellulase (23 mg/g of glucan) enzymes. During the enzyme hydrolysis temperature of reaction mixture was maintained at about 55° C. for about 48 h forming an enzyme treated stream. The sugar amounts formed after hydrolysis were about 2.9% w/w of glucose, about 1.55% w/w of xylose and 0.9% w/w of arabinose. The overall conversion of both cellulose and starch to glucose was about 84%. The enzyme treated stream was further subjected to fermentation with a recombinant *Saccharomyces cerevisiae* strain with prefermented quantity of 33 kg at about 32° C. for 72 h, during fermentation about 0.25 gm of glucoamylase (0.25 kg/ton of starch) was added for further conversion of starch to glucose. After 72 h about 2.1% w/w of ethanol was formed along with 0.1% w/w of xylose, 0.4% w/w of arabinose and nil glucose in the residual stream. This process afforded about 7.47 kg ethanol having a yield of 132 lit/MT from about 70 kg of solids from CFWC.

Example 2

A batch of 200 kg corn fiber wet cake (CFWC) with total solids of about 35% (that was about 70 kg of solids) was used as a feedstock. This feedstock was diluted with about 150 kg process water to make a slurry with about 20% w/w of solids comprising about 13.11% cellulose, about 11.18% xylan, about 9.22% arabinan and about 1.8% starch. Next, said slurry was soaked in about 1.39 kg of sulfuric acid (2% w/w) at ambient temperature for about 30 min forming acidic slurry. The temperature of said acidic slurry was then raised to about 70° C. using low pressure steam. Next, said acidic slurry was further mixed with 1.45 kg of sulfuric acid and 0.8 kg phosphoric acid (sulfuric acid-2% w/w and phosphoric acid-1% w/w) and treated at about 70° C. for about 30 min forming a second acidic slurry. Then it was passed through a jet cooker wherein temperature and pressure were maintained at about 145° C. and about 3.3 bar(g) for 26 min forming a pretreated stream. Post pre-treatment about 333 kg said pretreated stream was obtained having pH of about 1.2 with about 19.85% w/w total solids, about 1.4% w/w glucose, about 2.2% w/w xylose, about 1.8% w/w arabinose, about 0.40% w/w acetic acid, about 0.03% w/w HMF, and about 0.03% w/w furfural. Here the conversions of xylan to xylose, arabinan to arabinose and cellulose and starch to glucose in pre-treatment were 81%, 82% and 43% respectively. Then said pretreated stream was subjected to flashing forming a concentrated stream of reduced temperature. The pH of said concentrated stream was adjusted to about 5.5 using 4320 ml 40% w/v sodium hydroxide. Then said concentrated stream was treated with about 0.98 g of glucoamylase (0.75 kg/ton of starch) and about 211 g cellulase (23 mg/g glucan) enzymes. During enzyme hydrolysis temperature of reaction mixture was maintained at about 55° C. for about 48 h forming an enzyme treated stream. The sugar amounts formed after hydrolysis were about 3.05% w/w glucose, about 2.2% w/w xylose and 1.8% w/w arabinose. The overall conversion of both cellulose and starch to glucose was about 84% in said enzyme treated stream. The said enzyme treated stream was further subjected to fermentation by the recombinant *Saccharomyces cerevisiae* strain with prefermented quantity of 33 kg at about 32° C. for 72 h, during fermentation about 0.25 gm glucoamylase (0.25 kg/ton starch) was added for further conversion of starch to glucose. After 72 h about 2.8% w/w ethanol was formed along with 0.3% w/w xylose, 0.3% w/w arabinose and with having nil glucose in the residual stream. The process afforded about 10.1 kg ethanol having a yield of 180 L/MT from about 70 kg of solids from CFWC.

Example 3

A batch of 200 kg corn fiber wet cake (CFWC) with total solids of about 35% (that was about 70 kg of solids) was used as a feedstock. This feedstock was diluted with about 150 kg process water to make a dilution having solids about 20% w/w comprising about 12.06% cellulose, about 14.9% xylan, about 5.5% arabinan and about 5.9% starch. The temperature of said slurry was raised to about 70° C. using low pressure steam. Next, said slurry was mixed with about 1.45 kg sulfuric acid and about 0.8 kg phosphoric acid, (sulfuric acid 2% w/w and phosphoric acid 1% w/w and treated at about 70° C. for about 30 min forming acidic slurry. Next, said acidic slurry was passed through a jet cooker wherein temperature and pressure were maintained for about 145° C. and about 3.3 bar(g) for 26 min forming a pretreated stream. Post pre-treatment about 331 kg pretreated stream was obtained having pH of about 1.2, about 20.2% w/w total solids, about 0.5% w/w of glucose, about 1.7% w/w of xylose, about 0.7% w/w of arabinose, about 0.20% w/w of acetic acid, about 0.03% w/w of HMF and about 0.03% w/w of furfural. The conversion of xylan to xylose, arabinan to arabinose, and cellulose and starch to glucose in a pre-treatment were 48%, 53%, and 11% respectively. Then said pretreated stream was subjected to flashing reducing its temperature forming a concentrated stream. The pH of the concentrated stream was adjusted to about 5.5 using 4050 ml 40% w/v of sodium hydroxide. Then said concentrated stream was treated with about 3.08 g of glucoamylase (0.75 kg/ton of starch) and about 224 g cellulase (23 mg/g glucan) enzymes. During enzyme hydrolysis temperature of reaction mixture was maintained at about 55° C. for about 48 h. The sugar amounts formed after hydrolysis were about 3.5% w/w of glucose, about 1.7% w/w of xylose, and 0.2% w/w of arabinose. The overall conversion of both cellulose and starch to glucose was about 82% forming an enzyme treated stream. Next, said enzyme treated stream was subjected to fermentation with the recombinant *Saccharomyces cerevisiae* strain with prefermented quantity of 33 kg at about 32° C. for 72 h, during fermentation about 1.02 g glucoamylase (0.25 kg/ton starch) was added for further conversion of starch to glucose. After 72 h about 2.4% w/w of ethanol was formed along with 0.1% w/w of xylose, 0.6% w/w of arabinose, and nil glucose in the residual stream. The process afforded about 10.4 kg of ethanol having a yield of 150 L/MT from about 70 kg of solids from CWFC.

Example 4

A batch of 200 kg corn fiber wet cake (CFWC) with total solids of about 35% (that was about 70 kg of solids) was used as a feedstock. This feedstock diluted with about 150 kg process water to make a dilution with solids of about 20% w/w comprising about 12.6% cellulose, about 14.9% xylan, about 5.5% arabinan and about 5.5% starch. Next, said slurry was soaked in about 1.39 kg of sulfuric acid (2% w/w) at ambient temperature for about 30 min forming acidic slurry. The temperature of said acidic slurry was raised to about 70° C. using low pressure steam. Said acidic slurry was mixed with 1.45 kg of sulfuric acid and 0.8 kg phosphoric acid (sulfuric acid-2% w/w and phosphoric acid-1% w/w) for about 30 min forming a second acidic slurry. Said second acidic slurry was then passed through a jet cooker wherein temperature and pressure were maintained for about 145° C. and about 3.3 bar (g) for 26 min from a pretreated stream. Post pre-treatment about 332 kg pretreated stream was obtained having pH of about 1.2, about 19.7% w/w of total solids comprising about 1.8% w/w of glucose, about 2.9% w/w of xylose, about 1.1% w/w of arabinose, about 0.40% w/w of acetic acid, about 0.03% w/w of HMF and about 0.03% w/w of furfural. Here the conversions of xylan to xylose, arabinan to arabinose and cellulose and starch to glucose in pre-treatment were about 81%, 83% and 42% respectively. Then said pretreated stream was subjected to flashing reducing its temperature forming a concentrated stream. The pH of said concentrated stream was adjusted to about 5.5 using 4320 ml 40% w/v sodium hydroxide. Then said concentrated stream was treated with about 3.08 g of glucoamylase (0.75 kg/ton of starch) and about 224 g cellulase (23 mg/g glucan) enzyme forming an enzyme treated stream. During enzyme hydrolysis temperature of reaction mixture was maintained at about 55° C. for about 48 h. The sugar amounts formed after hydrolysis were about 3.65% w/w of gluclose, about 2.92% w/w of xylose and 1.12% w/w of arabinose. The overall conversion of both cellulose and starch to glucose was about 86%. The said enzyme treated stream was further subjected to fermentation with the recombinant *Saccharomyces cerevisiae* strain with prefermented quantity of 33 kg at about 32° C. for 72 h, during fermentation about 3.1 g glucoamylase (0.25 kg/ton starch) was added for further conversion of starch to glucose. After 72 h about 2.4% w/w of ethanol was formed along with 0.3% w/w of xylose, 0.3% w/w of arabinose having nil glucose in the residual stream. The process afforded about 13.6 kg ethanol having yield of 196 L/MT from 70 kg of solids from CFWC.

Example 5

To establish the morphological difference between soaked wet cake and native wet cake, the FEI quanta 200 3D dual beam environmental scanning electron microscope (ESEM) was used where electron source was a tungsten filament and acceleration of electron beam at a voltage of 30 KV under high vacuum. The native and soaked samples were prepared as per Examples 1 and 2. Said samples were dried under vacuum for 24 h prior to testing under the ESEM. The sample observation conditions and magnification were so adjusted that the morphology of cell walls could be studied determinatively. The ESEM images resolved at 20μ and 50μ, showed marked disruption of cell wall structures in the soaked samples. About 40% cell wall structures were broken after soaking the samples in acid. Said cell wall structures were coarser. The swelling of cell walls was observed in soaked wet cake whereas native wet cake showed rigid compact cell structure. The FIGS. 2A & 2B show the compact cell structure of native wet cake; while FIGS. 2C & 2D show the cell wall disruption (marked by arrows). The molecular structures of cell walls were changed after soaking leading to easy digestion of said native CFWC.

We claim:

1. A method for the production of ethanol from a mixed sugar medium comprising:
   a) conducting a yeast fermentation in a corn preparation forming a fermented stream;
   b) distilling ethanol from said fermented stream to produce a whole stillage;
   c) subjecting said whole stillage to solid liquid separation forming corn fiber wet cake and a liquid stream;
   d) preparing a slurry of said corn fiber wet cake and soaking it in sulfuric acid for a desired temperature and time period forming a first acidic slurry;
   e) preheating said first acidic slurry at a desired temperature and adding a mixture of sulfuric acid and phosphoric acid for a desired time period forming a second acidic slurry;
   f) cooking said second acidic slurry in a jet cooker at a desired temperature and time period forming a pretreated stream;
   g) flashing said pretreated stream in a reactor to reduce its temperature forming a concentrated stream;
   h) neutralizing said concentrated stream with sodium hydroxide and treating it with a mixture of enzymes that release fermentable sugars at a desired temperature and time period forming an enzyme treated stream;
   i) conducting a second yeast fermentation in said enzyme treated stream forming a second fermented stream; and
   j) distilling ethanol from said second fermented stream.

2. The method of claim 1, wherein said wet cake comprises cellulose between 10% and 15%, xylan between 12% and 16%, arabinan between 3% and 6%, and starch between 0.5% and 10% by weight.

3. The method of claim 1, wherein the concentration of sulfuric acid used for soaking is between 0.5% and 2% by weight of solids in said slurry.

4. The method of claim 1, wherein temperature at soaking is between 30° C. and 60° C.

5. The method of claim 1, wherein the time for soaking is between 20 and 40 minutes.

6. The method of claim 1, wherein the amount of said mixture of acids added to the first acidic slurry is between 0.5% and 4% by weight of solids in said first acidic slurry.

7. The method of claim 1, wherein the concentration of phosphoric acid in said mixture of acids is between 20% and 40% by weight.

8. The method of claim 1, wherein said first acidic slurry is heated to a temperature of between 70° C. and 90° C.

9. The method of claim 1, wherein said first acidic slurry is heated for a time period of between 5 and 40 minutes.

10. The method of claim 1, wherein said second acidic slurry is cooked at a temperature of between 140° C. and 150° C.

11. The method of claim 1, wherein said second acidic slurry is cooked for a time period of between 5 and 40 minutes.

12. The method of claim 1, wherein said pretreated stream comprises glucose between 0.2% and 2.5%, xylose between 1.5% and 3.5%, and arabinose between 0.5% and 1.5% by weight.

13. The method of claim 1, wherein said mixture of enzymes comprises cellulases, hemicellulases and starch hydrolysing enzymes.

14. The method of claim 1, wherein said concentrated stream is treated with said mixture of enzymes for a time period of between 30 and 72 h at a temperature of between 45° C. and 60° C.

15. The method of claim 1, wherein said enzyme treated stream comprises both C5 and C6 sugars.

16. The method of claim 1, wherein said enzyme treated stream comprises glucose between 1% and 4%, xylose between 1.5% and 3.5%, and arabinose between 0.5% and 1.5% by weight.

17. The method of claim 1, wherein said second yeast fermentation is conducted by an engineered yeast that converts both C5 and C6 sugars to ethanol.

18. The method of claim 1, wherein said recombinant yeast is *Saccharomyces cerevisiae*.

* * * * *